United States Patent [19]
Boothroyd et al.

[11] Patent Number: 5,859,196
[45] Date of Patent: *Jan. 12, 1999

[54] P30 PEPTIDES OF *TOXOPLASMA GONDII*

[75] Inventors: John Charles Boothroyd, Palo Alto; James Lawrence Burg, Foster City, both of Calif.; Lloyd H. Kasper, Norwich, Vt.

[73] Assignees: Trustees of the Leland Stanford Junior University, Hanover, N.H.; Trustees of Dartmouth College, Stanford, Calif.

[ * ] Notice: The term of this patent shall not extend beyond the expiration date of Pat. No. 5,629,414.

[21] Appl. No.: 461,296

[22] Filed: Jun. 5, 1995

Related U.S. Application Data

[62] Division of Ser. No. 182,673, Jan. 14, 1994, Pat. No. 5,629,414, which is a continuation of Ser. No. 1,215, Jan. 6, 1993, abandoned, which is a continuation of Ser. No. 616,693, Nov. 20, 1990, abandoned, which is a continuation of Ser. No. 166,384, Mar. 9, 1988, abandoned.

[51] Int. Cl.[6] .............................. C12N 15/63; C12N 5/10
[52] U.S. Cl. .................. 530/350; 435/172.3; 435/320.1; 435/69.7; 435/252.3; 435/69.1
[58] Field of Search .................... 530/300, 250; 424/191.1, 273.1; 435/7.1, 69.7, 69.1, 172.3, 320.1

[56] References Cited

FOREIGN PATENT DOCUMENTS

20027/88  2/1989  Australia .

OTHER PUBLICATIONS

Burg et al., *Molecular Genetics of Toxoplasma Gondii*, Journal of Cellular Biochemistry, Supplement 10A, UCLA Symposia on Molecular and Cellular Biology, Abstract C19, p. 122 (1986).

Burg et al., *Molecular cloning and Analysis of Genes Encoding Toxoplasma Gondii Antigens*, Journal of Cellular Biochemistry, Supplement 10A, UCLA Symposia on Molecular and Cellular Biology, Abstract C85, p. 145 (1986).

Burg et al., *Molecular Analysis of the Gene Encoding the Major Surface Antigens of Toxoplasma Gondii*, Journal of Immunology, vol. 141(10):3584–3591. (1988).

Kasper et al, *Identification of Stage–Specific Sporozoite Antigens of Toxoplasma Gondii by Monoclonal Antibodies1*, Journal of Immunology, vol. 132(1) :443–449, (1984).

Kasper et al., *An Unexpected Response to Vaccination with a Purified Major Membrane Tachyzoite Antigen (P30) of Toxoplasma Gondii*[1], Journal of Immunology, vol. 134(5):3426–2431, (1985).

Kasper et al., J. Immunology 130(5) : 2407–2412 (1983).

Sherman et al., J.Immunology 133(6) : 2818–2820 (1984).

*Primary Examiner*—Jasemine C. Chambers
*Assistant Examiner*—Karen M. Hauda
*Attorney, Agent, or Firm*—Cooley Godward LLP

[57] ABSTRACT

Genetic material encoding p30 and B1 peptides of *Toxoplasma gondii* has been isolated and characterized. This genetic material allows the production of peptides for use in diagnosis or immunization or can itself be directly used in hybridization assays.

9 Claims, 6 Drawing Sheets

FIG.1

```
1/1                                              31/11
GTT CTT CTC GGT TGT GTC ACA TGT GTC ATT GTC GTG TAA ACA CAC GGT TGT ATG TCG GTT
                                                            met ser val
61/21                                            91/31
TCG CTG CAC CAC TTC ATT ATT TCT TCT GGT TTT TTG ACG AGT ATG TTT CCG AAG GCA GTG
ser leu his his phe ile ile ser ser gly phe leu thr ser met phe pro lys ala val
121/41                                           151/51
AGA CGC GCC GTC ACG GCA GGG GTG TTT GCC GCG CCC ACA CTG ATG TCG TTC TTG CGA TGT
arg arg ala val thr ala gly val phe ala ala pro thr leu met ser phe leu arg cys
181/61                                           211/71
GGC GTT ATG GCA TCG GAT CCC CCT CTT GTT GCC AAT CAA GTT GTC ACC TGC CCA GAT AAA
gly val met ala ser asp pro pro leu val ala asn gln val val thr cys pro asp lys
241/81                                           271/91
AAA TCG ACA GCC GCG GTC ATT CTC ACA CCG ACG GAG AAC CAC TTC ACT CTC AAG TGC CCT
lys ser thr ala ala val ile leu thr pro thr glu asn his phe thr leu lys cys pro
301/101                                          331/111
AAA ACA GCG CTC ACA GAG CCT CCC ACT CTT GCG TAC TCA CCC AAC AGG CAA ATC TGC CCA
lys thr ala leu thr glu pro pro thr leu ala tyr ser pro asn arg gln ile cys pro
361/121                                          391/131
GCG GGT ACT ACA AGT AGC TGT ACA TCA AAG GCT GTA ACA TTG AGC TCC TTG ATT CCT GAA
ala gly thr thr ser ser cys thr ser lys ala val thr leu ser ser leu ile pro glu
421/141                                          451/151
GCA GAA GAT AGC TGG TGG ACG GGG CAT TCT GCT AGT CTC GAC ACG GCA GGC ATC AAA CTC
ala glu asp ser trp trp thr gly asp ser ala ser leu asp thr ala gly ile lys leu
481/161
ACA GTT CCA ATC GAG AAG TTC CCC GTG ACA ACG CAG ACG TTT GTG GTC GGT TGC ATC AAG
thr val pro ile glu lys phe pro val thr thr gln thr phe val val gly cys ile lys
541/181                                          571/191
GGA GAC GAC GCA CAG AGT TGT ATG GTC ACG GTG ACA GTA CAA GCC AGA GCC TCA TCG GTC
gly asp asp ala gln ser cys met val thr val thr val gln ala arg ala ser ser val
601/201
GTC AAT AAT GTC GCA AGG TGC TCC TAC GGT GCA GAC AGC ACT CTT GGT CCT GTC AAG TTG
val asn asn val ala arg cys ser tyr gly ala asp ser thr leu gly pro val lys leu
661/221                                          691/231
TCT GCG GAA GGA CCC ACT ACA ATG ACC CTC GTG TGC GGG AAA GAT GGA GTC AAA GTT CCT
ser ala glu gly pro thr thr met thr leu val cys gly lys asp gly val lys val pro
721/241                                          751/251
CAA GAC AAC AAT CAG TAC TGT TCC GGG ACG ACG CTG ACT GGT TGC AAC GAG AAA TCG TTC
gln asp asn asn gln tyr cys ser gly thr thr leu thr gly cys asn glu lys ser phe
781/261                                          811/271
AAA GAT ATT TTG CCA AAA TTA ACT GAG AAC CCG TGG CAG GGT AAC GCT TCG AGT GAT AAG
lys asp ile leu pro lys leu thr glu asn pro trp gln gly asn ala ser ser asp lys
841/281                                          871/291
GGT GCC ACG CTA ACG ATC AAG AAG GAA GCA TTT CCA GCC GAG TCA AAA AGC GTC ATT ATT
gly ala thr leu thr ile lys lys glu ala phe pro ala glu ser lys ser val ile ile
901/301                                          931/311
GGA TGC ACA GGG GGA TCG CCT GAG AAG CAT CAC TGT ACC GTG AAA CTG GAG TTT GCC GGG
gly cys thr gly gly ser pro glu lys his his cys thr val lys leu glu phe ala gly
961/321                                          991/331
GCT GCA GGG TCA GCA AAA TCG GCT GCG GGA ACA GCC AGT CAC GTT TCC ATT TTT GCC ATG
ala ala gly ser ala lys ser ala ala gly thr ala ser his val ser ile phe ala met
1021/341                                         1051/351
GTG ATC GGA CTT ATT GGC TCT ATC GCA GCT TGT GTC GCG TGA GTG ATC ACC GTT GTG CTC
val ile gly leu ile gly ser ile ala ala cys val ala OPA
1081/361                                         1111/371
ACT TCT CAA ATC GAC AAA GGA AAC ACA CTT CGT GCA GCA TGT GCC CCA TTA TAA AGA AAC
1141/381                                         1171/391
TGA GTT GTT CCG CTG TGG CTT GCA GGT GTC ACA TCC ACA AAA ACC GGC CGA CTC TAA ATA
1201/401
GGA GTG TTT CGC
```

FIG. 2a

B1-> 3-phase Translation

DNA sequence     2220 b.p.    GAATTCGTTCGA ... GCGGCTGAATTC    linear

B1 Gene

```
1/1                                           31/11
GAA TTC GTT CGA CAG AAA GGG AGC AAG AGT TGG GAC TAA ATC GAA GCT GAG ATG CTC AAA
 E   F   V   R   Q   K   G   S   K   S   W   D   *   I   E   A   E   M   L   K
  N   S   F   D   R   K   G   A   R   V   G   T   K   S   K   L   R   C   S   K
   I   R   S   T   E   R   E   Q   E   L   G   L   N   R   S   *   D   A   Q   S
61/21                                         91/31
GTC GAC CGC GAG ATG CAC CCG CAG AAG AAG GGC TGA CTC GAA CCA GAT GTG CTA AAG GCG
 V   D   R   E   M   H   P   Q   K   K   G   *   L   E   P   D   V   L   K   A
  S   T   A   R   C   T   R   R   R   R   A   D   S   N   Q   M   C   *   R   R
   R   P   R   D   A   P   A   E   E   G   L   T   R   T   R   C   A   K   G   V
121/41                                        151/51
TCA TTG CTG TTC TGT CCT ATC GCA ACG GAG TTC TTC CCA GAC GTG GAT TTC CGT TGG TTC
 S   L   L   F   C   P   I   A   T   E   F   F   P   D   V   D   F   R   W   F
  H   C   C   S   V   L   S   Q   R   N   G   V   S   S   Q   T   W   I   S   V   G   S
   I   A   V   L   S   Y   R   N   G   V   L   P   R   R   G   F   P   L   V   P
181/61                                        221/71
CGC CTC CTT CGT CCG TCG TAA TAT CAG GCC TTC TGT TCT GTT CGC TGT CTG TCT AGG GCA
 R   L   L   R   P   S   *   Y   Q   A   F   C   S   V   R   C   L   S   R   A
  A   S   F   V   R   R   N   I   R   P   S   V   L   F   A   V   C   L   *   G   H
   P   P   S   S   V   V   I   S   G   L   L   F   C   S   L   S   V   *   G   T
241/81                                        271/91
CCC TTA CTG CAA GAG AAG TAT TTG AGG TCA TAT CGT CCC ATG AAG TCG ACC ACC TGT TTC
 P   L   L   Q   E   K   Y   L   R   S   Y   R   P   M   K   S   T   T   C   F
  P   Y   C   K   R   S   I   *   G   H   I   V   P   *   S   R   P   P   V   S
   L   T   A   R   E   V   F   E   V   I   S   S   H   E   V   D   H   L   F   P
301/101                                       331/111
CTC TCT TCA CTG TCA CGT ACG ACA TCG CAT TCA AGG GAA GAG ATC CAG CAG ATC TCG TTC
 L   S   S   L   S   R   T   T   S   H   S   R   E   E   I   Q   Q   I   S   F
  S   L   H   C   H   V   R   H   R   I   Q   G   K   R   S   S   R   S   R   S
   L   F   T   V   T   Y   D   I   A   F   K   G   R   D   P   A   D   L   V   R
361/121                                       391/131
GTG TAT TCG AGA CAA GAG AGG TCC GCC CCC ACA AGA CGG CTG AAG AAT GCA ACA TTC TTG
 V   Y   S   R   Q   E   R   S   A   P   T   R   R   L   K   N   A   T   F   L
  C   I   R   D   K   R   G   P   P   P   Q   D   G   *   R   M   Q   H   S   C
   V   F   E   T   R   E   V   R   P   P   H   K   T   A   E   E   C   N   I   L   V
421/141                                       451/151
TGC TGC CTC CTC TCA TGG CAA ATG CCA GAA GAA GGG TAC GTG TTG CAT CAT AAC AAG AGC
 C   C   L   L   S   W   Q   M   P   E   E   G   Y   V   L   H   H   N   K   S
  A   A   S   S   H   G   K   C   Q   K   K   G   T   C   C   I   I   T   R   A
   L   P   P   L   M   A   N   A   R   R   R   V   R   V   A   S   *   Q   E   L
481/161                                       511/171
TGT ATT TCC CGC TGG CAA ATA CAG GTG AAA TGT ACC TCC AGA AAA GCC ACC TAG TAT CGT
 C   I   S   R   W   Q   I   Q   V   K   C   T   S   R   K   A   T   *   Y   R
  V   F   P   A   G   K   Y   R   *   N   V   P   P   E   K   P   P   S   I   V
   Y   F   P   L   A   N   T   G   E   M   Y   L   Q   K   S   H   L   V   S   C
```

FIG. 2b

```
541/181                                    571/191
GCG GCA ATG TGC CAC CTC GCC TCT TGG GAG AAA AAG AGG AAG AGA CGC TGC CGC TGT TTT
 A   A   M   C   H   L   A   S   W   E   K   K   R   K   R   R   C   R   C   F
  R   Q   C   A   T   S   P   L   G   R   K   R   G   R   D   A   A   A   V   L
   G   N   V   P   P   R   L   L   G   E   K   E   E   T   L   P   L   F   C
601/201                                    631/211
GCA AAT GAA AAG GAT TCA TTT TCG CAG TAC ACC AGG AGT TGG ATT TTG TAG AGC GTC TCT
 A   N   E   K   D   S   F   S   Q   Y   T   R   S   W   I   L   *   S   V   S
  Q   M   K   R   I   H   F   R   S   T   P   G   V   G   F   C   R   A   S   L
   K   *   K   G   F   I   F   A   V   H   Q   E   L   D   F   V   E   R   L   S
661/221                                    691/231
CTT CAA GCA GCG TAT TGT CGA GTA GAT CAG AAA GGA ACT GCA TCC GTT CAT GAG TAT AAG
 L   Q   A   A   Y   C   R   V   D   Q   K   G   T   A   S   V   H   E   Y   K
  F   K   Q   R   I   V   E   *   I   R   K   E   L   H   P   F   M   S   I   R
   S   S   S   V   L   S   S   R   S   E   R   N   C   I   R   S   *   V   I   E
721/241                                    751/251
AAA AAA ATG TGG GAA TGA AAG AGA CGC TAA TGT GTT TGC ATA GGT TGC AGT CAC TGA CGA
 K   K   M   W   E   *   K   R   R   *   C   V   C   I   G   C   S   H   *   R
  K   K   C   G   N   E   R   D   A   N   V   F   A   *   V   A   V   T   D   E
   K   N   V   G   M   K   E   T   L   M   C   L   H   R   L   Q   S   L   T   S
781/261                                    811/271
GCT CCC CTC TGC TGG CGA AAA GTG AAA TTC ATG AGT ATC TGT GCA ACT TTG GTG TAT TCG
 A   P   L   C   W   R   K   V   K   F   M   S   I   C   A   T   L   V   Y   S
  L   P   S   A   G   E   K   *   N   S   *   V   S   V   Q   L   W   C   I   R
   S   P   L   L   A   K   S   E   I   H   E   Y   L   C   N   F   G   V   F   A
841/281                                    871/291
CAG ATT GGT CGC CTG CAA TCG ATA GTT GAC CAC GAA CGC TTT AAA GAA CAG GAG AAG AAG
 Q   I   G   R   L   Q   S   I   V   D   H   E   R   F   K   E   Q   E   K   K
  R   L   V   A   C   N   R   *   L   T   T   N   A   L   *   K   N   R   R   R
   D   W   S   P   A   I   D   S   *   P   R   T   L   *   R   T   G   E   E   D
901/301                                    931/311
ATC GTG AAA GAA TAC GAG AAG AGG TAC ACA GAG ATA GAA GTC GCT GCG GAG ACA GCG AAG
 I   V   K   E   Y   E   K   R   Y   T   E   I   E   V   A   A   E   T   A   K
  S   *   K   N   T   R   R   G   T   Q   R   *   K   S   L   R   Q   R   R
   R   E   R   I   R   E   E   V   H   R   D   R   S   R   C   G   D   S   E   D
961/321                                    991/331
ACT GCG GAT GAC TTC ACT CCC GTC GCA CCA GCA GCA GAG GAG TGC CGG GCA AGA AAA TGA
 T   A   D   D   F   T   P   V   A   P   A   A   E   E   C   R   A   R   K   *
  L   R   M   T   S   L   P   S   H   Q   Q   Q   R   S   A   G   Q   E   N   E
   C   G   *   L   H   S   R   R   T   S   S   R   G   V   P   G   K   K   M   R
1021/341                                   1051/351
GAT GCC TAG AGG AGA CAC AGC GTG TTA TGA ACA AAT CTA TTG AGG TTT CGC GAA GAG GAG
 D   A   *   R   R   H   S   V   L   *   T   N   L   L   R   F   R   E   E   E
  M   P   R   G   D   T   A   C   Y   M   E   Q   I   Y   *   G   F   A   K   R   R
   C   L   E   E   T   Q   R   V   M   N   K   S   I   E   V   S   R   R   G
1081/361                                   1111/371
GGA ACA TAT TAT ATA CAG AAG AAG AAC AAG AGA CGT GCC GCA TGT CGC TAA GCC ATC GGA
 G   T   Y   Y   I   Q   K   K   N   K   R   R   A   A   C   R   *   A   I   G
  E   H   I   I   Y   R   R   R   T   R   D   V   P   H   V   A   K   P   S   E
   N   I   L   Y   T   E   E   E   Q   E   T   C   R   M   S   L   S   H   R   K
1141/381                                   1171/391
AGG GAT GCT CAG AAA ATG GCA CAG TAT CAC ATT ACA GTT CCG TTG ATT CGT CTG ATG GTG
 R   D   A   Q   K   M   A   Q   Y   H   I   T   V   P   L   I   R   L   M   V
  G   M   L   R   K   W   H   S   I   T   L   Q   F   R   *   F   V   *   W   *
   G   C   S   E   N   G   T   V   S   H   Y   S   S   V   D   S   S   D   G   D
```

FIG. 2c

```
1201/401                                          1231/411
ACG AAA GGG GAA GAA TAG TTG TCG CAC CAA AAC TGG CTA GTT GTT ATT TTG AAG AAG ACG
 T   K   G   E   E   *   L   S   H   Q   N   W   L   V   V   I   L   K   K   T
  R   K   G   K   N   S   C   R   T   K   T   G   *   L   L   F   *   R   R   R
   E   R   G   R   I   V   V   A   P   K   L   A   S   C   Y   F   E   E   D   E
1261/421                                          1291/431
AGA GAT GGA GTG AAC CAC CAA AAA TCG GAG AAA ATC GAT GGT GTC ACG TTT TTT GTC AGA
 R   D   G   V   N   H   Q   K   S   E   K   I   D   G   V   T   F   F   V   R
  E   M   E   *   T   T   K   N   R   R   K   S   M   V   S   R   F   L   S   D
   R   W   S   E   P   P   K   I   G   E   N   R   W   C   H   V   F   C   Q   T
1321/441                                          1351/451
CTT CAC TTT GTG CAG AAG CAT TGC CCG TCC AAA CTG CAA CAA CTG CTC TAG CGT GTT CGT
 L   H   F   V   Q   K   H   C   P   S   K   L   Q   Q   L   L   *   R   V   R
  F   T   L   C   R   S   I   A   R   P   N   C   N   N   C   S   S   V   F   V
   S   L   C   A   E   A   L   P   V   Q   T   A   T   T   A   L   A   C   S   S
1381/461                                          1411/471
CTC CAT TCC GTA CAG TCT TCA AAA ATA CAA AAG AGA ACA TTC CAG CAA CTT CTG CCT TTG
 L   H   S   V   Q   S   S   K   I   Q   K   R   T   F   Q   Q   L   L   P   L
  S   I   P   Y   S   L   Q   K   Y   K   R   E   H   S   S   N   F   C   L   C
   P   F   R   T   V   F   K   N   T   K   E   N   I   P   A   T   S   A   F   V
1441/481                                          1471/491
TTC TTT TAG CCT CAA TAG CAG GAT GAC GCC TCC CTC CTA TCT TTC AGC CAA CCC AGC AAA
 F   F   *   P   Q   *   Q   D   D   A   S   L   L   S   F   S   Q   P   S   K
  S   F   S   L   N   S   R   M   T   P   P   S   Y   L   S   A   N   P   A   N
   L   L   A   S   I   A   G   *   R   L   P   P   I   F   Q   P   T   Q   Q   T
1501/501                                          1531/511
CAC CGA CGA ACT CTC TGT AGA GTA ACA AAG AGA AGG CAA AAC GCG CCA TCA CGA ACA CTC
 H   R   R   T   L   C   R   V   T   K   R   R   Q   N   A   P   S   R   T   L
  T   D   E   L   S   V   E   *   Q   R   E   G   K   T   R   H   H   E   H   S
   P   T   N   S   L   *   S   N   K   E   K   A   K   R   A   I   T   N   T   R
1561/521                                          1591/531
GCA GAG ATG ATA CAG AGA CGT GTC ATC AGG ACA AGG TTG GTC GCT TAA TTT TCT GTA TAT
 A   E   M   I   Q   R   R   V   I   R   T   R   L   V   A   *   F   S   V   Y
  Q   R   *   Y   R   D   V   S   S   G   Q   G   Q   S   L   N   F   L   Y   I
   R   D   D   T   E   T   C   H   Q   D   K   V   G   R   L   I   F   C   I   *
1621/541                                          1651/551
AGC ATT TTT AGA ATG CAC CTT TCG GAC CTC AAC AAC CGT GCA AAA GGA TCG CCA CCT GGT
 S   I   F   R   M   H   L   S   D   L   N   N   R   A   K   G   S   P   P   G
  A   F   L   E   C   T   F   R   T   S   T   T   V   Q   K   D   R   H   L   V
   H   F   *   N   A   P   F   G   P   Q   Q   P   C   K   R   I   A   T   W   C
1681/561                                          1711/571
GTC TCT TCA AGC GTC AAA ACG AAC TAT CTG TAT ATC TCT CAA GGA GGA CTG GCA ACC TGG
 V   S   S   S   V   K   T   N   Y   L   Y   I   S   Q   G   G   L   A   T   W
  S   L   Q   A   S   K   R   T   I   C   I   S   L   K   E   D   W   Q   P   G
   L   F   K   R   Q   N   E   L   S   V   Y   L   S   R   R   T   G   N   L   V
1741/581                                          1771/591
TGT CGA CAA CAG AAC AGC TGC AGT CCG GAA ATA GAA AGC CAT GAG GCA CTC CAA CGG GCG
 C   R   Q   Q   N   S   C   S   P   E   I   E   S   H   E   A   L   Q   R   A
  V   D   N   R   T   A   A   V   R   K   *   K   A   M   R   H   S   N   G   R
   S   T   T   E   Q   L   Q   S   G   N   R   K   P   *   G   T   P   T   G   E
1801/601                                          1831/611
AGT AGC ACC TGA GGA GAT ACA AAC TGC TAA ACG GTC CGG GTG AAA CAA TAG AGA GTA CTG
 S   S   T   *   G   D   T   N   C   *   T   V   R   V   K   Q   *   R   V   L
  V   A   P   E   E   I   Q   T   A   K   R   S   G   *   N   N   R   E   Y   W
   *   H   L   R   R   Y   K   L   L   N   G   P   G   E   T   I   E   S   T   G
```

FIG. 2d

```
1861/621                                        1891/631
GAA CGT CGC CGC TAC TGC CCA GTT GTC ATG CCA TCG ACG TAG ACC CAG AAA TGA GGC GAG
 E   R   R   R   Y   C   P   V   V   M   P   S   T   *   T   Q   K   *   G   E
 N   V   A   A   T   A   Q   L   S   C   H   R   R   R   P   N   E   A   R
  T   S   P   L   L   P   S   C   H   A   I   D   V   D   P   E   M   R   R   E
1921/641                                        1951/651
AAA TTA ATA TTG TTA GTA AAG CAT TCA AAA AGT TCC GGT CGA GAG GCT AAA CCA CAA AAG
 K   L   I   L   L   V   K   H   S   K   S   S   G   R   E   A   K   P   Q   K
 N   *   Y   C   *   *   K   H   S   K   S   S   G   R   E   A   K   P   Q   K
  I   N   I   V   S   K   A   F   K   K   F   R   S   R   G   *   T   T   K   V
1981/661                                        2011/671
TGC AAA CCA TGC GCA GCC ATC AGC TTA ACA AAA GCA GTT GGT GAT GGT TGC CTC GAG TTC
 C   K   P   C   A   A   I   S   L   T   K   A   V   G   D   G   C   L   E   F
 A   N   H   A   Q   P   S   A   *   Q   K   Q   L   V   M   V   A   S   S   S
  Q   T   M   R   S   H   Q   L   N   K   S   S   W   *   W   L   P   R   V   P
2041/681                                        2071/691
CTT CTG AAA ATG GAT TAC TTC ATC AAC GAG CCC ACC ACG CAG AAT CAT GCT TTC CCA GTG
 L   L   K   M   D   Y   F   I   N   E   P   T   T   Q   N   H   A   F   P   V
 F   *   K   W   I   T   S   S   T   S   P   P   R   R   I   M   L   S   Q   C
  S   E   N   G   L   L   H   Q   R   A   H   H   A   E   S   C   F   P   S   A
2101/701                                        2131/711
CTA AAG CGT TTC TAA AGT AGC CGC ACA ATG CGG AAT GCT AAG GGG ATC GCC TAC GTA GCA
 L   K   R   F   *   S   S   R   T   M   R   N   A   K   G   I   A   Y   V   A
 *   S   V   S   K   V   A   A   Q   C   G   M   L   R   G   S   P   T   *   H
  K   A   F   L   K   *   P   H   N   A   E   C   *   G   D   R   L   R   S   T
2161/721                                        2191/731
CAT GTT GTG CCT CAC CCC CCA GCT CGT GCG CTC ATT CTC CTT TCG TGC GCG GCT GAA TTC
 H   V   V   P   H   P   P   A   R   A   L   I   L   L   S   C   A   A   E   F
 M   C   C   L   T   P   P   Q   L   V   R   S   F   S   F   R   A   R   L   *   N
  C   C   A   S   P   P   S   S   C   A   H   S   P   F   V   R   G   *   I
```

FIG. 2e

P30 PEPTIDES OF *TOXOPLASMA GONDII*

CROSS REFERENCE TO RELATED APPLICATIONS

This application is a division of U.S. application Ser. No. 08/182,673, filed Jan. 14, 1994, now U.S. Pat. No. 5,629,444, which is a continuation of U.S. application Ser. No. 08/001,215, filed Jan. 6, 1993, now abandoned, which is a continuation of U.S. application Ser. No. 07/616,693, filed Nov. 20, 1990, now abandoned, which is a continuation of U.S. application Ser. No. 07/166,384, filed on Mar. 9, 1988, now abandoned.

BACKGROUND OF THE INVENTION

1. Field of the Invention

This invention relates to the field of genetic engineering and more particularly to the identification and preparation of polynucleotide sequences and polypeptides useful for vaccine development and for detection of a toxoplasma infection by hybridization and immunological assays.

2. Description of the Background

Toxoplasmosis is caused by the protozoan parasite *Toxoplasma gondii*. The disease is traditionally associated with the developing fetus in whom it can cause severe neurological problems manifesting as hydrocephaly, mental retardation, or blindness. In healthy adults, the disease is typically mild producing few if any symptoms.

Recently, the number of toxoplasmosis cases has dramatically increased as a result of an increase in persons who are in some way immunodeficient, such as resulting from post-transplantation therapy, neoplastic disease, or acquired immunodeficiency syndrome (AIDS). In such immunodeficient patients, the parasite can cause encephalitis, a potentially fatal form of the disease.

The current means of diagnosing toxoplasmosis are costly, time consuming, of limited sensitivity, and associated with substantial risks to the patient. Conventional procedures involving serologic techniques are very often not reliable because of severe immune disfunction in AIDS patients and because of the recurrent nature of the disease. In pregnant women who are first tested for toxoplasmosis during pregnancy, it is critical to differentiate between current and past infection (currently done by comparing IgG and IgM titers over a period of time).

One problem that currently exists is obtaining sufficient quantities of suitable antigens both for the preparation of vaccines and for use as standards in immunological assays. Current techniques for providing antigen require the growth of protozoa in mice and the continual reinfection of new mice. Availability of a genetically-engineered polypeptide antigen capable of being used either as a vaccine or an immunological standard would alleviate numerous problems with the current source of antigen.

Furthermore, the methods of treatment for prevention of toxoplasma infection are currently limited. There are no commercial vaccines available for the control of toxoplasmosis. Treatment of the disease is generally initiated and maintained with a drug regimen involving a combination of pyrimethamine and sulfadiazine. However, toxicity due to the drug treatment can be significant so that prophylactic drug therapy is not recommended except where cysts have actually been detected.

Accordingly, there remains a need for the development of diagnostic assays that reliably detect low levels of toxoplasma infection and of materials useful for the production of vaccines.

SUMMARY OF THE INVENTION

The present invention provides genetic material encoding, among others, cell surface antigens of *T. gondii*. The genetic material can be used to produce polypeptides or proteins for use as vaccines or diagnostic reagents, or can be used themselves as probes in nucleic acid hybridization assays for the direct detection of toxoplasma infections. Specific genetic material and analytical techniques are disclosed in the following detailed description and the examples that follow.

BRIEF DESCRIPTION OF THE FIGURES

FIG. 2a shows an amino acid sequence and a corresponding nucleotide sequence for p30 DNA.

FIG. 2b–e shows amino acid sequences in three frames and a corresponding nucleotide sequence for B1 DNA.

DESCRIPTION OF SPECIFIC EMBODIMENTS

The present inventors have identified and obtained for the first time genetic material encoding specific proteins of the protozoan parasite *Toxoplasma gondii*. The specific antigens are the p30 and B1 antigens. The p30 antigen is a major surface antigen (see Kasper et al., *J. Imm.* (1983) 130:2407–2412) and can be used for the production of vaccines or diagnostic standards (the latter for use in immunoassays for detecting *T. gondii*). The function and location of the B1 antigen is unknown, but its multiple genomic nature makes it a particularly useful target for DNA hybridization assays. Accordingly, identification and isolation of the specified genetic material allows production of various biochemical components, such as antigens, diagnostic nucleic acid probes, and systems for producing the same, which find use in a variety of useful biological applications.

Since there is a known and definite correspondence between amino acids in a peptide and the DNA sequence that codes for the peptide, the DNA sequence of a DNA or RNA molecule coding for natural *T. gondii* proteins (or any of the modified peptides later discussed) will readily be understood as indicating particular amino acid sequences, and such exemplary sequences of nucleotides and amino acids are shown in FIGS. 2a and 2b.

Since the DNA sequence of the gene has been fully identified, it is possible to produce a DNA gene entirely by synthetic chemistry, after which the gene can be inserted into any of the many available DNA vectors using known techniques of recombinant DNA technology. Thus the present invention can be carried out using reagents, plasmids, and microorganism which are freely available and in the public domain at the time of filing of this patent application.

For example, nucleotide sequences greater than 100 bases long can be readily synthesized on an Applied Biosystems Model 380A DNA Synthesizer as evidenced by commercial advertising of the same (e.g., Genetic Engineering News, November/December 1984, p. 3). Such oligonucleotides can readily be spliced using, among others, the technique of preparing overlapping complementary sequences (e.g., 1–100 of coding strand, 0–50 and 51–150 of complementary strand, 101–200 of coding strand, etc.) followed by hybridizing and ligating the strands.

Furthermore, automated equipment is also available that makes direct synthesis of any of the peptides disclosed herein readily available. In the same issue of Genetic Engineering News mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition to the specific polypeptide sequences shown in FIGS. 2a and 2b peptide fragments based on these sequences and fragments representing minor variations thereof will have the biological activity of the various peptides. For example, fragments of the p30 peptide sequence that are capable of being recognized by immunoglobulins specific for the p30 antigen itself can readily be prepared and screened. Peptide synthesizers can be used to prepare small polypeptide fragments (e.g., less than 100 amino acids) or techniques of genetic engineering can be used to prepare larger fragments. A simple screening procedure that will identify suitable polypeptide fragments consists of preparing monoclonal antibodies to the p30 antigen, attaching the antibodies to an affinity column, and capturing peptide fragments that are retained by the bound antibody. Polyclonal antisera can be used instead of monoclonal antibodies if desired. The suitability of this technique has been demonstrated experimentally. A subsequence of the p30 sequence has been cloned and expressed as a β-galactosidase fusion product (identified as p30.5). The polynucleotide sequence encoding the p30.5 protein sequence begins at nucleotide number 582 and ends at nucleotide 996. The p30.5 polypeptide is reactive with polyclonal anti-p30 serum.

The ability to prepare and select appropriate immunologically active fragments from a larger protein is well known in the art and is described in a number of publications, including patents. See, for example, U.S. Pat. No. 4,629,783, which describes the preparation of immunologically active fragments of viral proteins.

One common variation is the preparation of a polypeptide of the invention in the form of a fused polypeptide. Such peptides are typically prepared by using the promoter region of a gene known to be expressed in a host and inserting nucleotides that encode all or a major portion of the amino acid sequence of the invention into the genetic sequence for the host protein. Examples of such fused proteins include the β-galactosidase fused protein discussed above.

Another technique for preparing immunologically active peptide fragments is to synthesize a series of amino acids of from 5–100 amino acids in length (or any intervening length, such as 10, 15, or any other multiple of 2, 3, or 5 in this range) and screen for immunological activity using an antiserum (or monoclonal antibody). The fragments would be selected along the entire length of the peptide to optimize cross-reactivity (e.g., a series of peptides 20 amino acids in length and comprising $AA_1$–$AA_{20}$ $AA_5$–$AA_{25}$, $AA_{10}$–$AA_{30}$, etc.). The selected fragment would then correspond to particularly useful corresponding nucleotide sequences that could be used to produce large amounts of the peptide for use as described herein.

In addition, minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e., a conservative replacement) will not have a major effect on the biological activity of the resulting molecule, especially if the replacement does not involve an amino acid at a binding site or other site of biologic activity. Whether a change results in a functioning peptide can readily be determined by direct analysis for function in an immunization or in a diagnostic test that relies on immunogenic specificity. Examples of this process are described later in detail. Peptides in which more than one replacement has taken place can readily be tested in the same manner. Preferred peptides differ at no more than 12, more preferably no more than 5, amino acids in any contiguous group of 20 amino acids. Standard conservative groups of amino acids are shown in parenthesis using the one-letter amino acid code: non-polar (A,V,L,I,P,M); aromatic (F,T,W); uncharged polar (G,S,T,C,N,Q); acidic (D,E); basic (K,R,H). The aromatic groups are sometimes considered to belong to the broader-defined nonpolar (F,W) or uncharged polar (T) groups.

Other DNA molecules that code for such peptides can readily be determined from the list of codons in Table 2 and are likewise contemplated as being equivalent to the DNA sequence of FIGS. 2a and 2b. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

TABLE 2

| Genetic Code | | | |
|---|---|---|---|
| Alanine(Ala) | GCL | Leucine(Leu) | XTY |
| Arginine(Arg) | WGZ | Lysine(Lys) | AAJ |
| Asparagine(Asn) | AAK | Methionine(Met) | ATG |
| Aspartic acid(Asp) | GAK | Phenylalanine(Phe) | TTK |
| Cysteine(Cys) | TGK | Proline(Pro) | CCL |
| Glutamic acid(Glu) | GAJ | Serine(Ser) | QRS |
| Glutamine(Gln) | CAJ | Threonine(Thr) | ACL |
| Glycine(Gly) | GGL | Tryptophan(Trp) | TGG |
| Histidine(His) | CAK | Tyrosine(Tyr) | TAK |
| Isoleucine(Ile) | ATM | Valine(Val) | GTL |
| | | Termination signal | TAJ |
| | | Termination signal | TGA |

Key:
Each 3-letter triplet represents a trinucleotide of DNA having a 5' end on the left and a 3' end on the right. The letters stand for the purine or pyrimidine bases forming the nucleotide sequence.

A = adenine  Y = A, G, C, or T if X is C
C = cytosine  Y = A or G if X is T
G = guanine  W = C or A if Z is C or T
J = A or G  W = C if Z is C or T
K = T or C  Z = A, G, C, or T if W is G
L = A, T, C, or G  Z = A or G if W is A
M = A, C, or T  QR = TC if S is A, G, C, or T
T = Thymine  QR = AG if S is T or C
X = T or C if Y is A or G  S = A, G, C, or T if QR is TC
X = C if Y is C or T  S = T or C if QR is AG In addition to the specific nucleotides listed in FIGS. 2a and 2b, DNA (or corresponding RNA) molecules of the invention can have additional nucleotides preceeding or following those that are specifically listed. For example, poly A can be added to the 3'-terminal, short (e.g., fewer than 20 nucleotides) sequence can be added to either terminal to provide a terminal sequence corresponding to a restriction endonuclease site, stop codons can follow the peptide sequence to terminate translation, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation or detection of DNA from biological sources.

Peptides of the invention can be prepared for the first time as homogeneous preparations, either by direct synthesis or by using a cloned gene or a fragment thereof as described herein. The p30 peptide was previously enriched by affinity chromatography, but the resulting material was not free of all other toxoplasma materials. By "homogeneous" is meant, when referring to a peptide or DNA sequence, that the primary molecular structure (i.e., the sequence of amino acids or nucleotides) of substantially all molecules present in the composition under consideration is identical. The term "substantially" as used in the preceding sentence preferably means at least 95% by weight, more preferably at least 99% by weight, and most preferably at least 99.8% by weight. The presence of fragments derived from entire molecules of the homogeneous peptide or DNA sequence, if present in no more than 5% by weight, preferably 1% by weight, and more preferably 0.2% by weight, is not to be considered in determining homogeneity since the term "homogeneous" relates to the presence of entire molecules (and fragments thereof) have a single defined structure as opposed to mixtures in which several molecules of similar molecular weight are present but which differ in their primary molecular structure. The term "isolated" as used herein refers to pure peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acylamide gel) but not obtained either as pure substances or as solutions. The term "pure" as used herein preferably has the same numerical limits as "substantially" immediately above. The phrase "replaced by" or "replacement" as used herein does not necessarily refer to any action that must take place but to the peptide that exists when an indicated "replacement" amino acid is present in the same position as the amino acid indicated to be present in a different formula (e.g., when leucine is present at amino acid 3 of p30 instead of valine).

Salts of any of the peptides described herein will naturally occur when such peptides are present in (or isolated from) aqueous solutions of various pHs. All salts of peptides having the indicated biological activity are considered to be within the scope of the present invention. Examples Include alkali, alkaline earth, and other metal salts of carboxylic acid residues, acid addition salts (e.g., HCl) of amino residues, and zwitter ions formed by reactions between carboxylic acid and amino residues within the same molecule.

The invention has specifically contemplated each and every possible variation of polynucleotide that could be made by selecting combinations based on the possible codon choices listed in FIGS. 2a and 2b and Table 2, and all such variations are to be considered as being specifically disclosed.

Although genes and corresponding proteins can be prepared by the totally synthetic techniques discussed above, in preferred embodiments of the invention genetic information is obtained from natural sources and identified as described herein. The genetic material is first obtained in the form of a gene library, using any of numerous existing techniques. The first of these is to randomly shear genomic DNA and insert this sheared material into expression vectors. If enough recombinants are generated, there is a good probability of having at least one recombinant in the population which is expressing a fusion protein corresponding to the antigen of interest. In practice, for a genome the size of $T.$ $gondii$ (about $7 \times 10^7$ bp), at least $5 \times 10^6$ independent recombinants are needed. This allows for the entire genome to be represented by recombinants where at least one insert will exist with one of its ends falling within any 10-base-pair region. Allowing for only 1 in 6 such insertions being in the correct orientation and reading frame, functional recombinants should exist in such a library with fusions corresponding to every 60 base pairs.

Such a library was generated in the laboratory of the inventors and screened with serum from an infected mouse. Among the recombinants expressing determinants reactive with the serum was one which was found at above average frequency. This recombinant, arbitrarily termed B1, has been characterized as follows.

The B1 gene is 2.2 kilobases (kb) long and is tandemly repeated about thirty-five times in a head-to-tail manner. There are no extensive open reading frames based on the complete sequence of the gene. This suggests that either only a short polypeptide product is encoded or that there are introns in this gene. A B1 cDNA has been isolated which begins at nucleotide 411 and ends at nucleotide 1384, as shown in the following sequence:

```
411
 |
 AAC ATT CTT GTG ... GTG TTC GTC TCC  (polyA)
                                   |
                                  1384
```

One intron is identified in the genomic sequence as beginning at nucleotide 456 and ending at nucleotide 843 as shown in the following sequence:

```
456
 |
 GTA CGT GTT ... GTG TAT TCG CAG
                              |
                             843
```

Accordingly, an open reading frame is present that begins with the 5'-end of the CDNA clone (frame 3), switches to frame 1 at the beginning of the new exon (thereby maintaining the ORF), and ends at nucleotide 1020.

A second strategy of preparing gene libraries is to make complementary DNA (cDNA) copies of the total mRNA population of the parasite and to clone these as recombinant molecules in expression vectors. Other investigations carried out by the present inventors indicated that introns were present within the coding regions of other $T.$ $gondii$ genes. Although introns do not preclude use of sheared genomic DNA, they increase the number of recombinants which must be screened and make further analyses substantially complicated. Based on this result, use of a EDNA library to obtain $T.$ $gondii$ genes is preferred.

Polyclonal antisera to p30 can be used to screen a CDNA library in order to locate the p30 gene. Recombinants initially identified in this manner have been found to contain different genes, implying that at least some fortuitous cross-reaction with anti-p30 sera occurs. The true p30 gene can be obtained by preparing antisera against each of the fusion proteins obtained in the initial screening. These sera are then used in Western blot analyses against a lysate of $T.$ $gondii$. Only antisera from the fusion product of the p30 gene will show reactivity predominantly or exclusively to p30.

A clone obtained in the manner described above has been fully sequenced. This sequence was used to isolate other cDNA clones. Together, these sequences can be used to predict the complete protein-coding sequence of the gene as shown in FIGS. 2a and 2b. A hydrophobicity analysis of the predicted amino acid sequence is set forth in FIG. 1. The primary translation product has a predicted $M_r$ of 36,210 kD. It also has a probable hydrophobic signal peptide at its N-terminus, as expected for a surface antigen. It has one predicted N-glycosylation site (residue 267) consistent with investigations of previous workers which have indicated that the p30 protein may be a glycoprotein. Finally, it has a hydrophobic C-terminus which is not followed by any charged residues. This is apparently diagnostic of a process originally reported in trypanosomes whereby the hydrophobic polypeptide segment is replaced by a glycolipid anchor. Such a process is now known to occur for major surface antigens of Leishmania and Plasmodium as well.

The gene encoding the p30 antigen can be used for the production of full or modified peptides using standard techniques of manipulating and growing uni-cellular microorganisms. Antigens which are candidates for vaccine development and/or diagnostic reagents will include those recognized by serum from infected patients. Additionally, any of the genetic sequences can be used as probes in hybridization assays.

Although the techniques set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of *T. gondii* protein can be enhanced by including multiple copies of the gene in a transformed host, by selecting a vector known to reproduce in the host, thereby producing large quantities of protein from exogeneous inserted DNA (such as pUC8; ptac12; pIN-III-ompA1, 2, or 3; pOTS; pAS1; or pKK223-3), or by any other known means of enhancing peptide expression.

In all cases, a *T. gondii* protein will be expressed when the DNA sequence is functionally inserted into the vector. By "functionally inserted" is meant in proper reading frame and orientation, as is well understood by those skilled in the art. Typically, a gene will be inserted downstream from a promoter and will be followed by a stop codon, although production as a hybrid protein (possibly followed by cleavage) may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

The implications of the present invention are significant in that unlimited supplies of *T. gondii* proteins and genetic material of the invention will become available for use in the development of hybridization assays or in any other type of assay utilizing these materials as a reagent for use in diagnosis, immunization, therapeutics, and research. Methods of using genetic material in a hybridization assay are disclosed in U.S. application Ser. No. 080,479, filed Jul. 31, 1987, and commonly assigned, which is herein incorporated by reference. Transferring the *T. gondii* cDNA which has been isolated to other expression vectors will produce constructs which improve the expression of a *T. gondii* polypeptide in *E. coli* or express the polypeptide in other hosts.

Particularly contemplated is the isolation of genes from these and related organisms that express *T. gondii* protein using oligonucleotide probes based on the principal and variant nucleotide sequences disclosed herein. Such probes can be considerably shorter than the entire sequence but should be at least 10, preferably at least 14, nucleotides in length. Intermediate oligonucleotides from 20 to 500, especially 30 to 200, nucleotides in length provide particularly specific and rapid-acting probes. Longer oligonucleotides are also useful, up to the full length-of the gene. Both RNA and DNA probes can be used.

In use, the probes are typically labelled in a detectable manner (e.g., with $^{32}P$, $^{3}H$, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known. The B1 gene is a particularly desirable target of hybridization, as it is already present in multiple copies.

Although probes are normally used with a detectable label that allows easy identification, unlabeled oligonucleotides are also useful, both as precursors of labeled probes and for use in methods that provide for direct detection of double-stranded DNA (or DNA/RNA), such as absorption onto nitrocellulose. Accordingly, the term "oligonucleotide probe" refers to both labeled and unlabeled forms.

The invention now being generally described, the same will be better understood by reference to the following examples which are provided for purposes of illustration only and are not to be considered limiting of the invention unless so specified.

EXAMPLES

The genetic material having the sequences set forth in FIGS. 2*a* and 2*b* were isolated as described below.

Materials and Methods

A. Parasite Material

Most of the work described here uses the RH strain of *Toxoplasma gondii* which is the most commonly used laboratory strain amongst Toxoplasma researchers (Pfefferkorn et al., *Exp. Parasitol.* (1976) 39:365–376). Due to its long history of continuous passage in the laboratory, it is highly virulent in animals and grows rapidly in culture making it ideal for obtaining large amounts of material. However, it has lost the ability to go through the complete sexual cycle in cats. Accordingly, more recent isolates, "C" and "P" strains which retain full biological function but grow more slowly (Pfefferkorn et al., *J. Parasitol.* (1977) 63:158–159 and Ware et al., *Infect. Immun.* (1987) 55:778–783), were also used.

Parasites were generally grown in vitro in monolayers of cultured human foreskin fibroblasts (HFF). Typically, using the RH strain, infected cultures were maintained by seeding uninfected monolayers at about a 1:50 dilution every 48–72 hours. This yields about $10^9$ parasites from three T175 flasks of infected cultures. Parasites were harvested just as lysis occurred by passage of trypsinized cells through a syringe and removal of HFF debris by column chromatography, as described in Hoshino-Shimizu et al., *J. Parasitol* (1980) 60:989–991.

B. Gene Libraries

Three gene libraries for *T. gondii* were constructed in the inventors' laboratory. Unless otherwise noted, all libraries comprise λgt11 recombinants constructed by adding EcoRI linkers to methylated inserts and cloning into the EcoRI site of the vector. These are:

1. λRHg1, a library of needle-sheared genomic DNA from RH strain.
2. CRHg1, a library of partially Sau3A digested RH genomic DNA inserted into the BamHI site of the cosmid vector c2XB (Bates et al., *Gene* (1983) 26:137–146).
3. λRHc2, a cDNA library of RH strain tachyzoite mRNA prepared in the inventors' laboratory.

Libraries were constructed and manipulated as described in Huynh et al., In D. M. Glover (ed): DNA Cloning, Oxford: IRL Press (1985) pp. 49–78.

C. Antibodies

1. Monoclonal Anti-Toxoplasma

Monoclonal antibodies to two polypeptide antigens of the RH strain of *T. gondii* were used. Together with their specificities, these are:

a. 7B8: against p30, the major surface antigen of about 30 kD (Kasper et al., *J. Imm.* (1983) 130: 2407–2412).

2. Polyclonal Anti-Toxoplasma

In addition to antisera raised by the inventors, collaborators provided the following antisera:

a. HC1 . . . HC10: human sera from infants congenitally infected with *T. gondii*.
b. HA: human sera from infected human adults.
c. Rp30: rabbit antisera to purified p30 (prepared by immunoadsorption to mcAb 7B8).
d. RTL1 and RTL2: rabbit antisera to lysates of *T. gondii* RH strain tachyzoites.

Results

A. Surface Antigen p30

We used polyclonal antisera to p30 (Rp30) to screen our cDNA library, λRHc2. Several recombinants were identified on the first screen, and of these, three were chosen for further examination based on the strength and reproducibility of the positive signal. The three recombinants were compared by isolating the inserts and using each as a hybridization probe against the other and in Southern blot analyses of digested genomic DNA. From this, it became clear that the three recombinants represent different genes, implying that at least two were due to fortuitous cross-reaction with the anti-p30 sera. Sequence and Southern blot analyses confirmed their distinct coding functions. To determine which was the true p30 gene, rabbit antisera was prepared to each fusion protein by excising the appropriate band from an acrylamide gel and injecting this into a rabbit. These sera were then used in Western blot analyses against a lysate of *T. gondii*. Only antisera to one clone, λTc30.5, showed reactivity to p30. This sera also showed reactivity to no other material in the lysate. That this was indeed p30, rather than a comigrating material, is evident from the reactivity of the antisera with purified p30. The other two clones are clearly distinct genes and presumably only fortuitously cross-reactive.

Figure 1:
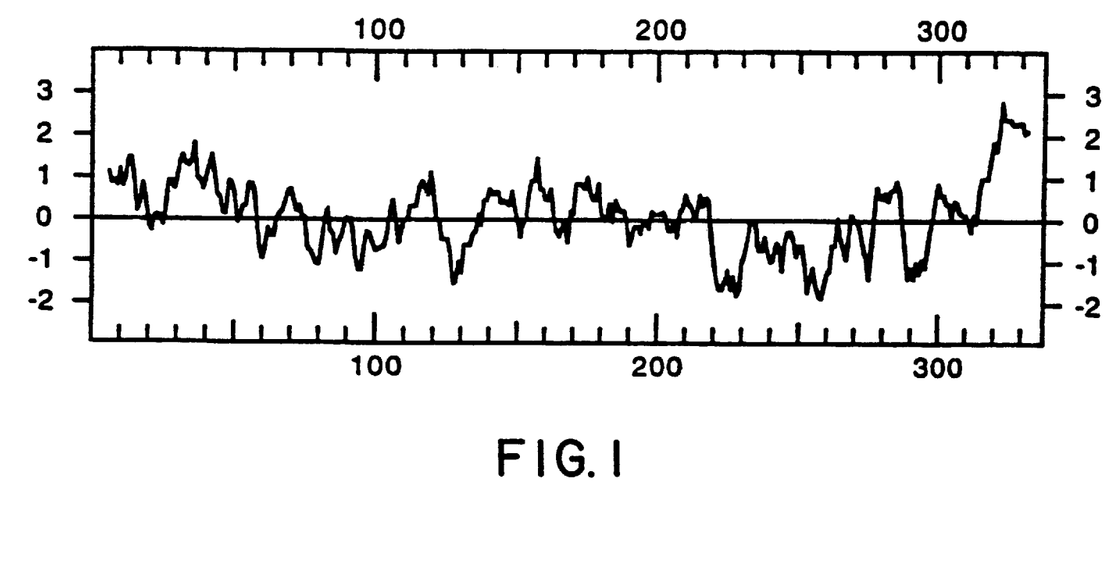
FIG. 1 shows a hydropathy plot of p30 using DNA Strider™ computer program which is based on a Kyte-Doolittle analysis.

The λTc30.5 clone was fully sequenced and used to isolate other cDNA clones which have also been sequenced. From these, a complete sequence for the p30 coding region has been derived (see FIGS. 2a and 2b). FIG. 1 shows a hydrophobicity analysis of the predicted amino acid sequence. The primary translation product has a predicted $M_r$ of 36,210 kD although the precise amino terminus cannot be determined without direct protein sequencing. It also has a probable hydrophobic signal peptide at its N-terminus, as expected for a surface antigen. It has one predicted N-glycosylation site (residue 267) consistent with prior results indicating that p30 may be a glycoprotein. Finally, it has a hydrophobic C-terminus which is not followed by any charged residues. This is apparently diagnostic of the process originally reported in trypanosomes whereby the hydrophobic polypeptide segment is replaced by a glycolipid anchor. Such a process is now known to occur for major surface antigens of Leishmania and Plasmodium.

Using the predicted amino acid sequence, the sizes of cyanogen bromide fragments can be predicted. The data indicate two large fragments, one of which has a tyrosine. Using $^{125}$I-labeled p30, cyanogen bromide generates a single large fragment (by polyacrylamide gel electrophoresis) of the predicted size (11 kD) along with several small fragments. Moreover, the polypeptide sequence predicts substantial hydrophobicity for the protein as a whole as previously indicated for p30 by charge-shift immunoelectrophoresis. These results further confirm that the recombinant encodes p30.

The presumptive p30 gene is present in one copy per haploid genome and encodes a mRNA of 1.5 kb. Based on the signal intensity of the Northern analyses (the band is readily apparent in 0.25 hr) and abundance of cDNAs for this gene in the cDNA library (at least 20 plaques per 10,000 recombinant phage), it is an abundant message as would be expected of a protein present at about 3% of total cellular protein.

B. Repeat Gene B1

A mouse antisera raised against a lysate of *T. gondii* was used to screen the sheared genomic library λRHg1 as a means of identifying possible antigen-encoding genes prior to the availability of the polyclonal antisera. Several recombinants were identified, most of which, it transpired, represented the same gene (here, arbitrarily referred to as B1), which exists as a 2.2 kb tandem repeat in the *T. gondii* genome. A partial CDNA clone (including poly A tail) has been identified from the λRHc2 library and sequenced. A part of the complete open reading frame has been identified (at least one intron is so far apparent from comparing the genomic and cDNA sequence); the transcriptional orientation and approximate end points of transcription unit are indicated. Despite repeated attempts, we have been unable to identify the product of the recombinant phage which is responsible for the reactivity to antisera (such reactivity is easily reproducible on phage lifts but has never been observed in Western blots of the induced lysogen). This lack of reactivity has precluded identifying the in vivo antigen because no bacterial product can be identified for purification and "antibody selection" has been unsuccessful (presumably because of insufficient avidity and/or titer of the anti-B1 antibodies in the serum. Significantly, the gene is conserved (as judged by Southern blot analyses of EcoRI digests) in the genome of all four other *T. gondii* strains analyzed, including a recent isolate from an AIDS patient.

The repeated nature of this gene enhances its utility as a target for direct diagnosis by hybridization assays, such as those described in prior application, Ser. No. 080,479, filed Jul. 31, 1987.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of producing a p30 protein of *Toxoplasma gondii* comprising introducing into a host cell an expression vector comprising a DNA sequence encoding the amino acid sequence set forth in FIG. 2a, and transcriptional control sequences, said DNA sequence and transcriptional control sequences having been functionally inserted into said expression vector, and culturing said transformed host cell under conditions that allow expression of said p30 protein of *Toxoplasma gondii*.

2. The method of claim 1, wherein said DNA sequence comprises the nucleotide sequence set forth in FIG. 2a.

3. The method of claim 1, wherein said p30 protein has a hydropathy corresponding to that of FIG. 1.

4. A method of preparing a p30 fusion protein of *Toxoplasma gondii* comprising
   (a) introducing into a host cell an expression vector comprising:
      (i) a DNA sequence consisting of nucleotides 582–996 of the DNA sequence set forth in FIG. 2a;
      (ii) a DNA sequence encoding a polypeptide of interest linked to said DNA sequence of (i); and
      (iii) transcriptional control sequences, said sequences of (i), (ii) and (iii) having been functionally inserted into said expression vector; and
   (b) culturing said transformed host cell under conditions that allow expression of said p30 fusion of *Toxoplasma gondii*.

5. The method of claim 4, wherein said polypeptide of interest is β-galactosidase.

6. An isolated p30 polypeptide of *Toxoplasma gondii* consisting of the amino acid sequence set forth in FIG. 2a.

7. A recombinant fusion protein comprising a polypeptide encoded by nucleotides 582–996 of the DNA sequence set forth in FIG. 2a fused to a polypeptide of interest.

8. The fusion protein of claim 7, wherein said polypeptide of interest is β-galactosidase.

9. A composition comprising the isolated p30 polypeptide of claim 6 and a pharmaceutically acceptable carrier.

* * * * *